United States Patent [19]

Fickenscher

[11] Patent Number: 5,554,527
[45] Date of Patent: Sep. 10, 1996

[54] AGENT FOR THE STORAGE AND SUSPENSION OF CELLS, ESPECIALLY ERYTHROCYTES

[75] Inventor: Karl Fickenscher, Marburg, Germany

[73] Assignee: Behringwerke Aktiengesellschaft, Marburg, Germany

[21] Appl. No.: 871,575

[22] Filed: Apr. 20, 1992

Related U.S. Application Data

[63] Continuation of Ser. No. 606,922, Oct. 31, 1990, abandoned.

[30] Foreign Application Priority Data

Nov. 24, 1989 [DE] Germany ............................ 39 38 907.3

[51] Int. Cl.$^6$ ............................... C12N 5/00; A01N 1/02; G01N 33/53; G01N 31/00
[52] U.S. Cl. .......................... 435/240.1; 436/8; 436/18; 435/2; 435/7.8; 424/601; 252/380; 252/397; 514/774; 514/822
[58] Field of Search ........................... 435/240.1, 2, 7.8; 436/8, 18; 424/601; 252/380, 397; 514/774, 822

[56] References Cited

U.S. PATENT DOCUMENTS

| | | | |
|---|---|---|---|
| 4,102,810 | 7/1978 | Armstrong | 436/16 |
| 4,356,172 | 10/1982 | Nakao et al. | |
| 4,489,162 | 12/1984 | Hawkins et al. | 435/2 |
| 4,572,899 | 2/1986 | Walker | 436/18 |
| 4,704,352 | 11/1987 | Miripol et al. | |
| 4,755,461 | 7/1988 | Lawson et al. | 436/18 |
| 4,769,318 | 9/1988 | Hamasaki et al. | |
| 4,874,690 | 10/1989 | Goodrich et al. | 435/2 |

FOREIGN PATENT DOCUMENTS

| | | |
|---|---|---|
| WO81/02239 | 8/1981 | WIPO. |
| WO86/00809 | 2/1986 | WIPO. |
| WO87/04072 | 7/1987 | WIPO. |
| WO89/02274 | 3/1989 | WIPO. |

OTHER PUBLICATIONS

Bernard Horowitz et al., "Stabilization of Red Blood Cells by the Plasticizer, Diethylhexylphthalate," Vox Sang. 48:150–155 (1985).
A. Heaton et al., "Use of Adsol Preservation Solution for Prolonged Storage of Low Viscosity AS-1 Red Blood Cells," British Journal of Haematology, 57:467–478 (1984).
Penny RHC et al. British Veterinary Journal (1970) vol. 126 pp. 383–389.
Davis et al. Microbiology, 3rd Ed. 1980 Harper & Row p. 394.
Rose, et al. Methods in Immunodiagnosis John Wiley & Sons, 1973 pp. 206–207.
Bach, et al. Immunology, Second Edition John Wiley & Sons, 1982 p. 252.

Primary Examiner—Esther M. Kepplinger
Assistant Examiner—Choon P. Koh
Attorney, Agent, or Firm—Finnegan, Henderson, Farabow, Garrett & Dunner, L.L.P.

[57] ABSTRACT

The invention relates to an agent for the preservation, storage and suspension of cells, especially erythrocytes, which contains a chelating agent for multiply charged metal ions, in addition to other substances known to those skilled in the art, such as, for example, electrolytes and sugars.

6 Claims, 3 Drawing Sheets

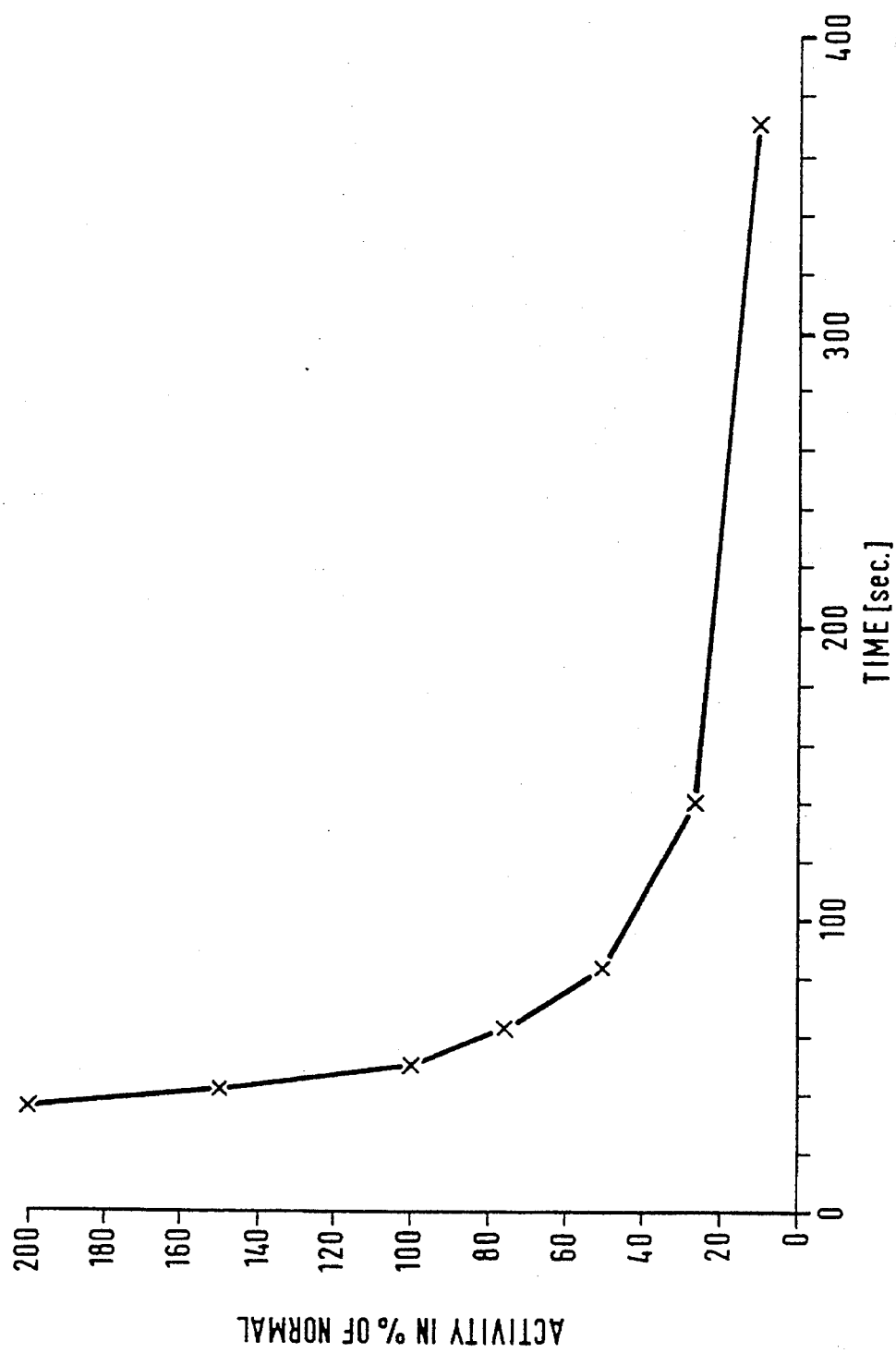

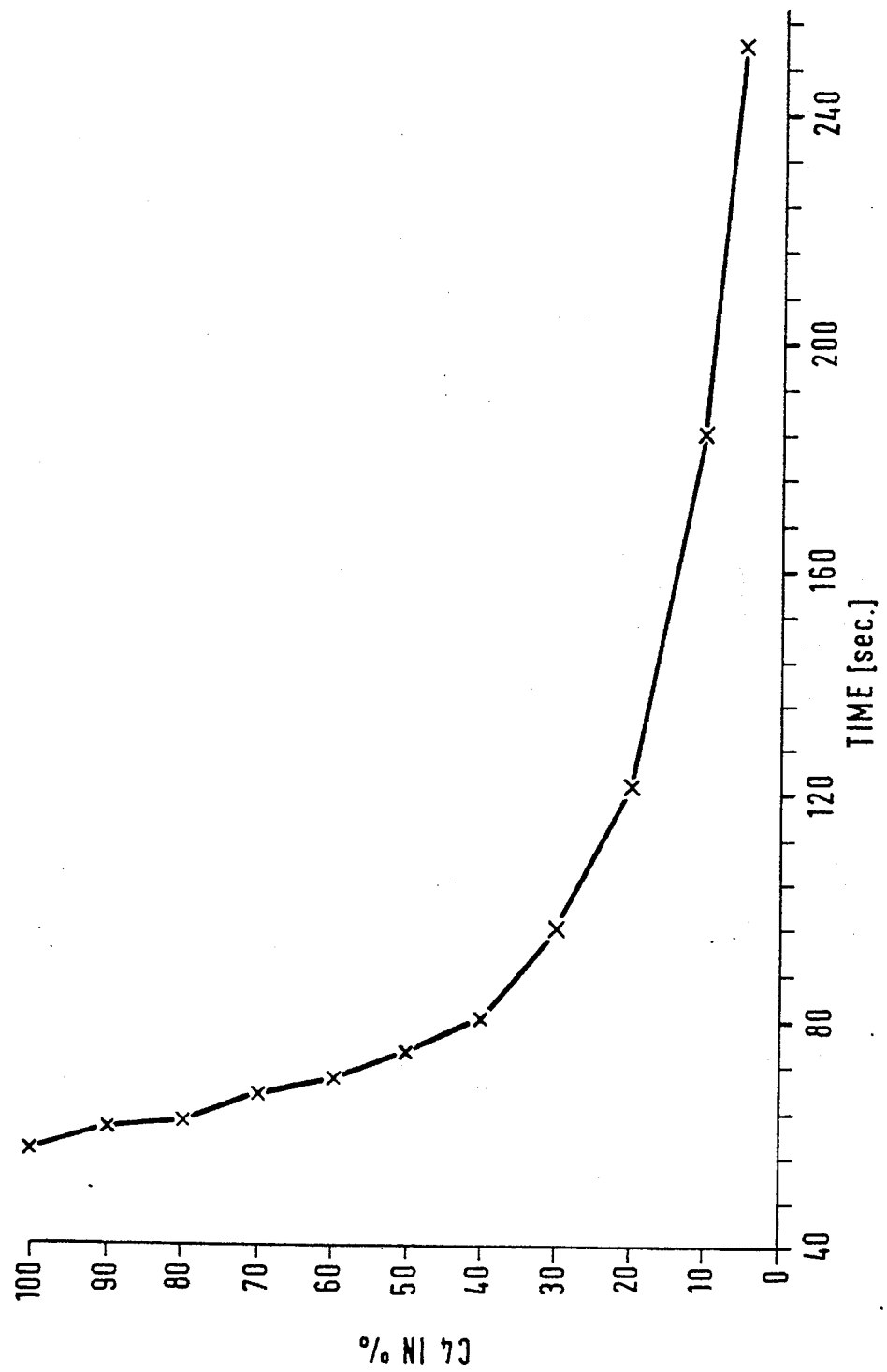

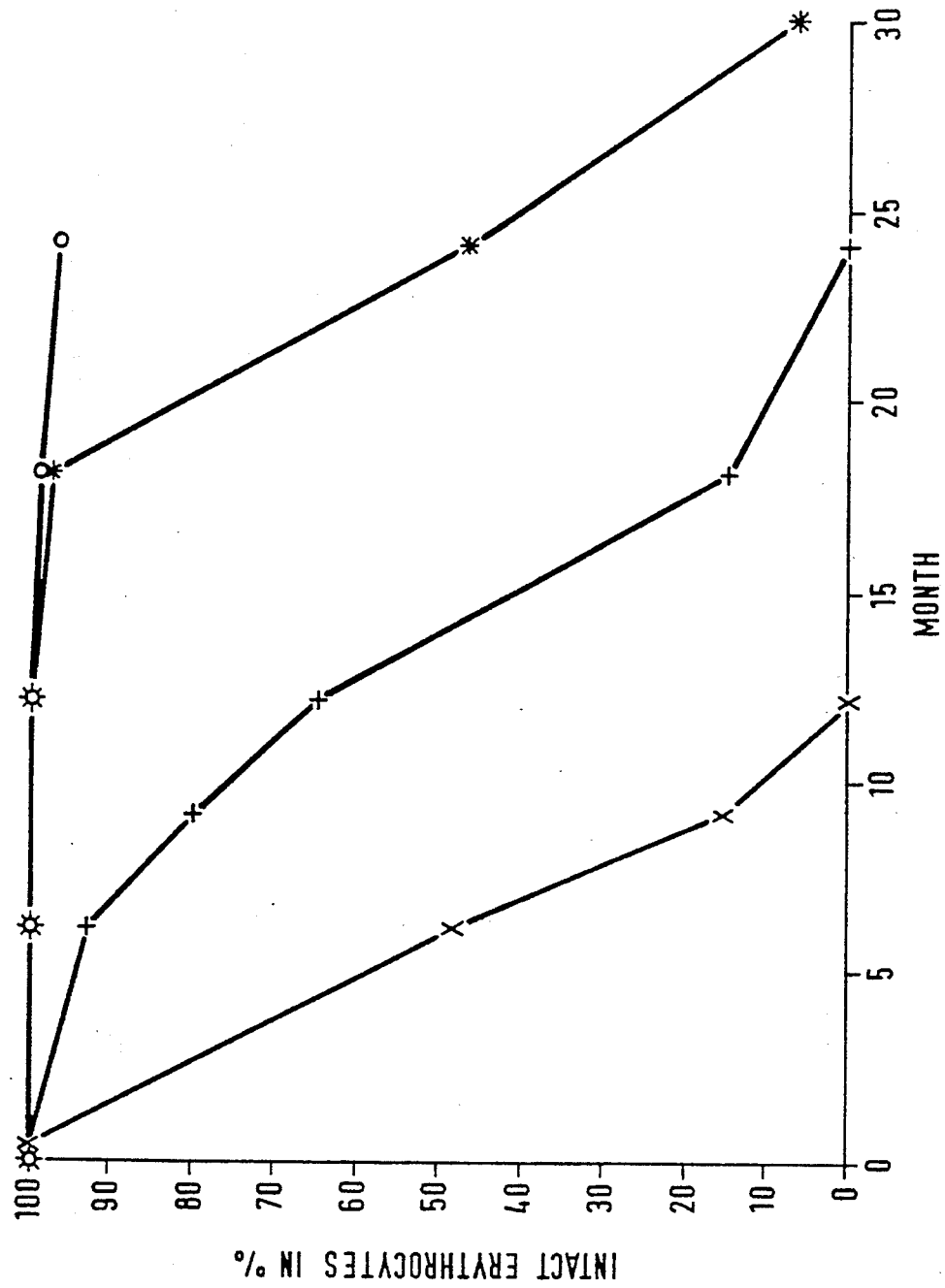

AGENT FOR THE STORAGE AND SUSPENSION OF CELLS, ESPECIALLY ERYTHROCYTES

This application is a continuation of application Ser. No. 07/606,922, filed Oct. 31, 1990, now abandoned.

The invention relates to an agent for the preservation, storage and suspension of cells, especially erythrocytes, which contains a chelating agent for multiply charged metal ions, in addition to other substances known to those skilled in the art, such as, for example, electrolytes and sugars.

Required for the preparation of reagents for the determination of particular parameters (for example complement determination) are erythrocytes which have been isolated from anticoagulated whole blood and stabilized.

Erythrocyte concentrates are prepared by removal of plasma from whole blood (stored blood) as part of blood component therapies. These concentrates are currently used widely in therapy, for example in cases of anemia or where there is an indication for administration of erythrocytes. In order to adjust the erythrocyte concentrates to a physiologically tolerated viscosity it is necessary to add a diluent solution with which it is also possible to introduce the substances needed to increase the storage stability.

Various agents are suitable for the suspension and storage of cells, especially erythrocytes. Thus, for example, WO 81/02239 describes a solution which contains adenine, mannitel, glucose or fructose and sodium chloride. WO 86/00809 describes a solution which contains adenine, mannitel, glucose, potassium citrate and ammonium chloride or ammonium acetate. WO 87/04072 describes a solution which can contain L-amine acids or derivatives thereof, fatty acids or derivatives thereof, intermediate products of glycolysis such as phosphoenol pyruvate and analogs thereof, nucleosides such as adenosine or guanosine, adenosine monophosphate and derivatives thereof, ammonium, glycogen, acetyl-CoA and derivatives, allantoin, 4-ethyl oxaloacetate, phenylethyl biguanide and analogs, quercetin, cobalt sulfate, nickel sulfate, magnesium chloride, manganese chloride and various inhibitors of diphosphoglycerate phosphatase as additions to the standard components anticoagulant, sugar alcohol, glucose and sodium chloride. WO 89/02274 describes a solution which contains glucose, sodium chloride, potassium chloride, calcium chloride, magnesium sulfate, sodium phosphate, sodium citrate and sodium bicarbonate. U.S. Pat. No. 4,267,269 describes a solution which, besides adenine, contains the sugar alcohol mannitol, glucose or fructose and sodium chloride. U.S. Pat. No. 4,356,172 describes a solution which contains adenine or inosine, sucrose or lactose, and citric acid or a salt thereof. U.S. Pat. No. 4,704,352 describes a solution which has a pH of below 7.0 to stabilize blood cells and contains adenine, mannitol, dextrose, sodium chloride and L-ascorbate 2-phosphate. U.S. Pat. No. 4,769,318 describes the stabilization and activation of blood before transfusion by means of a derivative of phosphoenol pyruvate, and adenine, a saccharide (sucrose, maltose, galactose or mannitol), citric acid or the sodium salt thereof (also EP 0,275,198). EP 0,099,315 describes a phosphate-buffered solution which contains adenine, glucose, sucrose and sodium chloride. EP 0,100,419 describes a phosphate-buffered solution which contains adenine and/or guanosine, a sugar alcohol (sorbitol or xylitol), glucose or fructose, sodium chloride and colloids. EP 0,301,250 describes a phosphate-buffered solution which contains adenine and/or guanosine, a sugar alcohol (sorbitol, mannitol or xylitol), glucose or fructose, sodium chloride and colloids. (See also DE-A 37 22 984). DE 3,220,232 describes a process and a solution for stabilizing blood platelets by the use of iodoacetamide, of an iminoacetic acid and of a bacteriostatic agent. DE-A 3,225,408 describes a solution which contains adenine or guanosine, a sugar alcohol (sorbitol or xylitol), glucose or fructose. Furthermore, Heaton et al. (in British Journal of Haematology 57, 467–478, 1984) describe a solution (ADSOL(R)) essentially composed of adenine, mannitol, dextrose and sodium chloride for the stabilization of erythrocytes. Likewise known is the stabilizing action of the plasticizer diethylhexyl phthalate which is toxic for humans (Horowitz B. et al. Vox Sang. 48, 150–155, 1985).

Although the addition of such suspending solutions to erythrocyte concentrates has improved the survival rate and thus the storage stability of erythrocytes, these improvements were too small to meet the stringent requirements, for example on the minimum shelf lives of a diagnostic aid. It was not possible either to use these to prepare a reagent ready for use because the adjusted erythrocyte concentration and the properties of the erythrocytes changed during storage.

Thus the object of the invention was to improve the survival rate, and thus the storage stability of cells, or the hemolysis rate of erythrocytes.

The present invention now relates to agents for the suspension, preservation and storage of biologically active cells or cell constituents, especially erythrocytes, where the agent contains a chelating agent for multiply charged metal ions, in addition to other substances known to those skilled in the art, such as, for example, anticoagulants, electrolytes, sugars and sugar alcohols, in a buffered aqueous solution. It has been found, surprisingly, that cells, especially erythrocytes, have a considerably higher survival rate and greatly reduced hemolysis rate when they are stored in a solution of this type.

Chelating agents for multiply charged metal ions are compounds known to those skilled in the art. Chelating agents for doubly charged metal ions are preferably used, the use of ethylenediaminetetraacetate (EDTA), ethylene glycol bisaminoethyl ether tetraacetate (EGTA) or oxalic acid is particularly preferred, and the use of EGTA is very particularly preferred. The chelating agents are employed in concentrations of 0 to 100 mmol/l, preferably of 0.1 to 50 mmol/l and particularly preferably of 2–10 mmol/l.

Particularly suitable electrolytes are sodium, potassium and magnesium salts in the form of the chlorides, sulfates or citrates.

Preferably used as sugars are sucrose and fructose, and as sugar alcohol are mannitol, glucose and sorbitol.

Other suitable additives are, inter alia, colloids, in which case gelatin and polygeline are preferred.

Preferred anticoagulants are heparin and citrate. The stability can be further improved by the addition of an antibiotic which is not harmful to cells, such as, for example, Kathon DP® (Röhm & Haas) or chloramphenicol.

Kathon DP is sold by Röhm & Haas and is composed of 5-chloro-2-methyl-3[2H]isothiazolone (CAS 26172-55-4) and 2-methyl-3 [2H]isothiazolone (CAS 2682-20-4).

The agent according to the invention can additionally contain other substances which are known to those skilled in the art from the class of nucleosides (for example adenosine or guanosine), from the class of purine bases (for example adenine) or intermediate products and substrates of glycolysis. Other additives which are used in the known agents can also be combined with the agent according to the invention.

The beneficial properties of a solution of this type can be further improved by adding adenosine triphosphate (ATP) and/or employing a sodium salt of phosphoric acid as second buffer substance.

Buffer substances are all physiologically tolerated buffer substances, and HEPES or a water-soluble phosphate is preferably used.

The agents of Example 2 and 3 are very particularly preferred.

A typical solution ready for use has the following composition, for example: per liter of solution, dissolved in distilled water, 0 to 100 mmol of glucose, 20 to 200 mmol of sodium chloride, 0 to 50 mmol of potassium chloride, 0 to 10 mmol of magnesium chloride, 2 to 100 mmol of HEPES, 0 to 100 mmol of Na phosphate, 0.1 to 50 mmol of ethylenediaminetetraacetate (EDTA), ethylene glycol bisaminoethyl ether tetraacetate (EGTA) or oxalacetic acid, preferably EGTA, 0 to 20,000 units of heparin, 0 to 5 g of gelatin, 0 to 50 mmol of ATP and 0 to 1 g of Kathon or chloramphenicol, pH 5.0 to 9.0, preferably 6.5 to 7.5 and very particularly preferably 6.8 when Kathon is used and 7.4 when chloramphenicol is used. The composition of the solution is preferably such that it is approximately isotonic.

The normal procedure for using these solutions is such that a citrate- or heparin-stabilized whole blood of human or animal origin is prepared. The whole blood is centrifuged and the plasma, including the boundary layer to the erythrocytes, is removed. The erythrocytes are subsequently washed twice in the buffer solution without ATP. The washed erythrocytes are subsequently adjusted to the desired concentration with the complete buffer and are stored at 2°–8° C. or used immediately.

The examples which follow serve to illustrate the invention but do not restrict it in any way.

EXAMPLE 1

Preparation of an erythrocyte suspension for diagnostic purposes 300 ml of blood are taken in a citrated receiver as anticoagulant under sterile conditions from a sheep. The whole blood is centrifuged at 1000×g for 15 min to remove the plasma. The plasma is aspirated off, including the boundary layer to the cell pellet, and the erythrocytes are taken up in the same volume (based on the volume of the erythrocyte pellet) of washing buffer (stabilizing agent as described in Example 3 without EGTA, ATP and heparin) and mixed. The cells are subsequently spun down as above, and the washing step is repeated once more. To adjust to the correct concentration of erythrocytes, the latter are resuspended in the same volume of stabilizing agent as described in Example 3, and the absorbance at 578 nm is determined on a 1:100 dilution in the stabilizing buffer. The desired dilution is calculated from this value, and the erythrocytes are diluted to the appropriate value. The suspended erythrocytes are subsequently bottled in portions. It was found that suspensions prepared in this way can be stored at 2°–8° C. for 2 years without the occurrence of any relevant hemolysis or any loss of diagnostic utilizability (Table 1).

TABLE 1

| Erythrocyte storage time | Hemolysis % | Lysis time in the complement assay for a normal plasma sec |
|---|---|---|
| 0 | 0 | 45 |
| 1 month | 0 | 44 |
| 6 months | 0 | 44 |
| 12 months | 0 | 43 |
| 18 months | 1 | 42 |
| 24 months | 3 | 45 |

EXAMPLE 2

Preparation of a suspending solution 80 mmol of glucose, 150 mmol of sodium chloride, 10 mmol of potassium chloride, 0.5 mmol of magnesium chloride, 10 mmol of HEPES, 10 mmol of EDTA, 1 g of gelatin and 2 mmol of ATP are weighed out and dissolved in 900 ml of distilled water. Then 10,000 units of heparin and 0.05% Kathon are added. After the pH has been adjusted to 6.8, the solution is made up to 1 liter with distilled water. The solution is subsequently sterilized by filtration through membrane filters with a pore width of 0.2 μm under pressure.

EXAMPLE 3

Preparation of a modified suspending solution 80 mmol of glucose, 150 mmol of sodium chloride, 10 mmol of potassium chloride, 0.5 mmol of magnesium chloride, 10 mmol of HEPES, 40 mmol of $NaH_2PO_4$, 2 mmol of EGTA, 1 g of gelatin and 2 mmol of ATP are weighed out and dissolved in 900 ml of distilled water. Then 10,000 units of heparin and 0.5 g of Kathon are added. After the pH has been adjusted to 6.8, the solution is made up to 1 liter with distilled water. The solution is subsequently sterilized by filtration through a membrane filter with a pore width of 0.2 μm under pressure.

FIG. 3 shows the time course of hemolysis over 2 years at 4° C. compared with solutions of the state of the art (80 mmol/l glucose, 150 mmol/l NaCl, 10 mmol/l HEPES, 10 mmol/l KCl, 0.5 mmol/l adenine, 0.1% gelatin) (x—x); state of the art and with the chelator EDTA (+—+); with the solution of Example 2 (*—*), and with the solution of Example 3 (▫—▫).

EXAMPLE 4

Procedure for determining C4 activity using the erythrocyte suspension

Preparation of the reagent: 0.5 ml of the erythrocyte suspension is mixed with 5 ml of a solution which contains antibodies against the erythrocytes and heated to 37° C. The reagent is then ready for use. Procedure for the determination: 10 μl of sample are mixed with 100 μl of a C4-deficient plasma. 1 ml of the reagent is pipetted into this and the time which elapses while the absorbance at 578 nm decreases by 0.1 A, owing to lysis of the erythrocytes, is determined. Comparison of the resulting time with the values from a calibration plot constructed analogously beforehand yields the content of functionally active C4.

FIG. 2 shows the dependence of the lysis time of the stabilized erythrocytes on the activity of C4 in the sample.

EXAMPLE 5

Procedure for determining the total complement activity using the erythrocyte suspension Preparation of the reagent: 0.5 ml of the erythrocyte suspension is mixed with 5 ml of a solution which contains antibodies against the erythrocytes and heated to 37° C. The reagent is then ready for use. Procedure for the determination: 1 ml of the reagent is pipetted into 100 μl of sample, and the time which elapses while the absorbance at 578 nm decreases by 0.1 A, owing to lysis of the erythrocytes, is determined. Comparison of the resulting time with the values from a calibration plot constructed analogously beforehand with dilutions of a pooled plasma with isotonic saline yields the complement activity of the sample.

FIG. 1 shows the dependence of the lysis time of the stabilized erythrocytes on the total complement activity in the sample.

I claim:

1. A method for the preservation and storage of erythrocytes in a suspendable form comprising the steps of: a) separating erythrocytes from blood containing said erythrocytes; and b) suspending the separated erythrocytes in an aqueous solution buffered at a pH of 5 to 9, and containing 2 to 50 mmol/l of a chelating agent for the chelation of multiply charged ions, wherein the aqueous solution in step (b) further comprises per liter 3–100 mmol of glucose or fructose, 20–200 mmol of sodium chloride, 10–50 mmol of potassium chloride, 0.5–10 mmol of magnesium chloride, 2–100 mmol of HEPES, 0–100 mmol of sodium phosphate, 10,000–20,000 units of heparin, 1–5 grams of gelatin or polygeline, 2–50 mmol of ATP and 0–1 g of 5-chloro-2-methyl-3[2H]isothiazolone and 2-methyl-3 isothiazolone or chloramphenicol, and wherein the erythrocytes are preserved for at least six months.

2. The method of claim 1 wherein the chelating agent is selected from the group consisting of EDTA, EGTA, and oxalic acid.

3. The method as claimed in claim 1 wherein the pH of the aqueous solution is 6.5 to 7.5.

4. An aqueous solution obtained by the method of claim 1 containing suspendable or suspended erythrocytes.

5. A method for the determination of complement activity which comprises (a) mixing a sample to be tested for complement activity with the aqueous solution of claim 4 and a solution which contains antibodies which specifically bind erythrocytes, and (b) determining lysis time of the erythrocytes as a measure of the complement activity of said sample.

6. A method for the determination of the activity of inhibitors of the complement system which comprises (a) mixing a sample to be tested for the activity of inhibitors with the aqueous solution of claim 4, a solution which contains antibodies which specifically bind erythrocytes, and complement, and (b) determining lysis time of the erythrocytes as a measure of the activity of the inhibitors of said sample.

* * * * *